(12) United States Patent
Blume et al.

(10) Patent No.: US 7,341,835 B2
(45) Date of Patent: Mar. 11, 2008

(54) METHODS OF ANALYSIS OF ALTERNATIVE SPLICING IN MOUSE

(75) Inventors: John E. Blume, Danville, CA (US); Alan J. Williams, Albany, CA (US)

(73) Assignee: Affymetrix, Inc., Santa Clara, CA (US)

( * ) Notice: Subject to any disclaimer, the term of this patent is extended or adjusted under 35 U.S.C. 154(b) by 563 days.

(21) Appl. No.: 11/036,317

(22) Filed: Jan. 13, 2005

(65) Prior Publication Data

US 2005/0214823 A1    Sep. 29, 2005

Related U.S. Application Data

(60) Provisional application No. 60/536,639, filed on Jan. 13, 2004.

(51) Int. Cl.
  *C12Q 1/68* (2006.01)
  *C12M 3/00* (2006.01)
  *C12M 1/34* (2006.01)
  *C07H 21/04* (2006.01)

(52) U.S. Cl. ............ 435/6; 435/287.2; 435/91.1; 536/23.1; 536/24.3

(58) Field of Classification Search ............ None
  See application file for complete search history.

(56) References Cited

OTHER PUBLICATIONS

Hu et al. (Genome Research, vol. 11, pp. 1237-1245, 2001).*

* cited by examiner

*Primary Examiner*—Juliet C. Switzer
(74) *Attorney, Agent, or Firm*—Sandra E. Wells

(57) ABSTRACT

The invention provides nucleic acid sequences which are complementary, in one embodiment, to a wide variety of mouse genes. The invention provides the sequences in such a way as to make them available for a variety of analyses. In one embodiment the nucleic acid sequences provided are present as an array of probes that may be used to measure gene expression of different mature RNA isoforms from at least 5,000 alternatively spliced mouse genes. As such, the invention relates to diverse fields impacted by the nature of molecular interaction, including chemistry, biology, medicine, pharmacology and medical diagnostics.

10 Claims, 3 Drawing Sheets

METHODS OF ANALYSIS OF ALTERNATIVE SPLICING IN MOUSE

RELATED APPLICATIONS

This application claims the benefit of U.S. Provisional Application No. 60/536,639, filed Jan. 13, 2004. The entire teachings of the above application are incorporated herein by reference in their entirety for all purposes.

FIELD OF THE INVENTION

The present invention provides pools of nucleic acid sequences and arrays of nucleic acid sequences that are useful for analyzing alternative splicing in nucleic acid samples derived from mice. The invention also provides a collection of probes that hybridize to regions of transcripts to detect splicing events. The invention relates to diverse fields, including genetics, genomics, biology, population biology, medicine, and medical diagnostics.

REFERENCE TO SEQUENCE LISTING

The Sequence Listing submitted on compact disk is hereby incorporated by reference. The machine format for the discs is IBM-PC, the operating system compatibility is MS-WINDOWS 2000, the file on the disc is titled "3654.1seqlist.txt", the file is 138 MB and the compact discs were created on Jan. 12, 2005.

BACKGROUND OF THE INVENTION

Recent genome-wide analysis of alternative splicing indicates that a large portion of human genes, probably more than half, have alternative splice forms. Alternative splicing provides the cell with a mechanism to generate multiple gene products from the same transcript, adding to the functional complexity of the genome. Recent reports that the human genome may contain many fewer genes than expected have resulted in the suggestion that alternative splicing may play a major role in the production of complexity.

The identities of the genes that are being expressed in a biological sample at any given time and the amount of expression of those genes provide a gene expression profile for that sample. The gene expression profile is an indication of the status of that sample. For example, different tissue types will have different gene expression profiles reflecting the expression of different genes and differences in the spliced forms of individual genes. Differences in expression profile may also be observed between samples from the same tissue type when one sample is diseased. High-throughput methods to analyze and detect expression of alternative splice forms, characterization of alternative splicing, and regulation of alternative splicing are an important research focus.

SUMMARY OF THE INVENTION

Methods and probe arrays for measurement of the expression of multiple isoforms of RNA from mouse genes are disclosed. In one aspect probe arrays that include more than 100,000 different probe sets are disclosed. Each probe set includes at least one probe, and preferably, 2, 4, 6 or more probes that are complementary to different regions of the same exon or a subsequence of an exon from a mouse gene. More than 100, 1000, or 10,000 different genes are interrogated by the array and each multi-exon gene is preferably interrogated by at least two probe sets and preferably by a probe set for each exon in the gene.

Arrays of probes that are complementary to alternatively spliced mouse transcripts are disclosed. In one embodiment an array comprising a plurality of nucleic acid probes, wherein each probe in the plurality of nucleic acid probes comprises one of the sequences listed in SEQ ID Nos. 1-991,174 and wherein the plurality of nucleic acid probes of the array comprises each of the sequences listed in SEQ ID Nos. 1-991,174 is disclosed. In another embodiment an array comprising SEQ ID Nos 1-495,673 is disclosed and in another embodiment an array comprising SEQ ID Nos. 495,674-991,174 is disclosed. The probes may be attached to a solid support which may be a membrane, a glass slide, or a bead, for example. The probes may be attached to a single solid support or to two or more solid supports.

In one embodiment a method of monitoring alternative splicing in a biological sample from a mouse is disclosed. Nucleic acid is isolated from the sample and amplified and labeled. The labeled sample is hybridized to the array and a hybridization pattern is detected and analyzed. The intensity of signal resulting from hybridization to probes on the array is used to monitor the levels of alternatively spliced forms of a gene. The hybridization patterns from two or more different samples may be compared to detect differences in alternative splicing.

In one embodiment labeled cDNA is hybridized to the array. In another embodiment labeled RNA is hybridized to the array. The labeled RNA may be complementary to the mRNA (antisense) in another embodiment the labeled RNA may be sense RNA.

Figure 1:
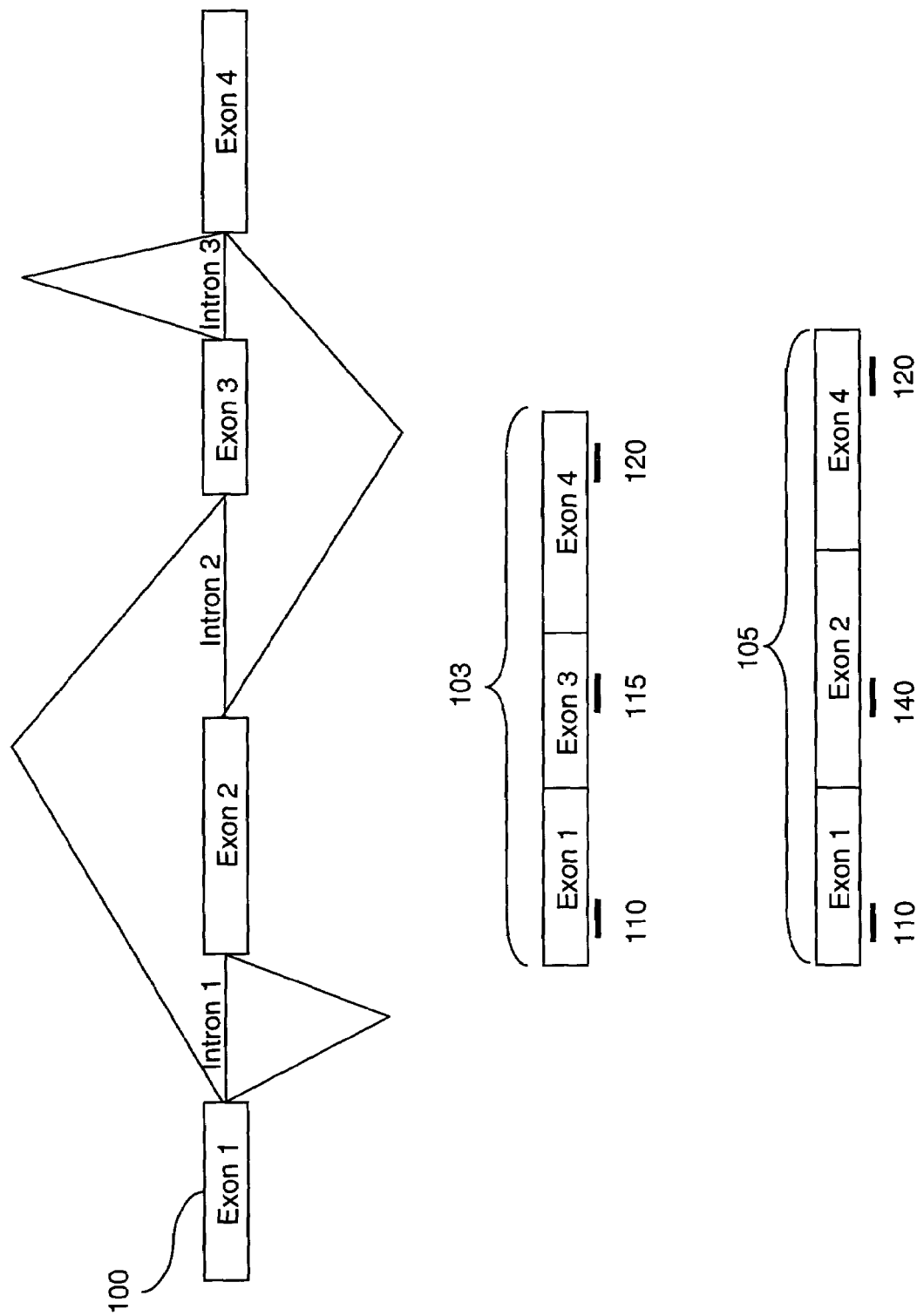
FIG. 1 shows an example of alternative splicing. Two mature RNA isoforms are generated differing in the inclusion of exons 2 and 3. The isoforms can be distinguished by probes that are specifically complementary to exon 2 or exon 3.

DETAILED DESCRIPTION OF THE PREFERRED EMBODIMENTS a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* 3$^{rd}$ Ed., W.H. Freeman Pub., New York, N.Y. and Berg et al. (2002) *Biochemistry*, 5$^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes. See also, Fodor et al., *Science* 251(4995), 767-73, 1991, Fodor et al., *Nature* 364(6437), 555-6, 1993 and Pease et al. *PNAS USA* 91(11), 5022-6, 1994 for methods of synthesizing and using microarrays.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Additional methods of genotyping, complexity reduction and nucleic acid amplification are disclosed in U.S. patent application Ser. Nos. 60/508,418, 60/468,925, 60/493,085, 09/920,491, 10/442,021, 10/654,281, 10/316,811, 10/646,674, 10/272,155, 10/681,773 and 10/712,616 and U.S. Pat. No. 6,582,938. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H.A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davis, *P.N.A.S*, 80: 1194 (1983). Methods and apparatus for carrying out repeated and controlled hybridization reactions have been described in U.S. Pat. Nos. 5,871,928, 5,874,219, 6,045,996 6,386,749, and 6,391,623.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. No. 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, (1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/063,559 (United States Publication No. US20020183936), 60/349,546, 60/376,003, 60/394,574 and 60/403,381.

b) Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

Preferred arrays typically comprise a plurality of different nucleic acid probes that are coupled to a surface of one or more substrates in different, known or determinable locations. Arrays have been generally described in, for example, U.S. Pat. Nos. 5,143,854, 5,445,934, 5,744,305, 5,677,195, 5,800,992, 6,040,193, 5,424,186 and Fodor et al., *Science*, 251:767-777 (1991).

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992.)

Arrays may be packaged in such a manner as to allow for diagnostic use or can be an all-inclusive device; e.g., U.S. Pat. Nos. 5,856,174 and 5,922,591. Preferred arrays are commercially available from Affymetrix (Santa Clara, Calif.) under the brand name GeneChip® and are directed to a variety of purposes, including genotyping and gene expression monitoring for a variety of eukaryotic and prokaryotic species.

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a l column by m row matrix of the building blocks to be added. The switch matrix is all or a subset of the binary numbers, preferably ordered, between l and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The phrase "massively parallel screening" refers to the simultaneous screening of from about 100, 1000, 10,000 or 100,000 to 1000, 10,000, 100,000, 1,000,000 or 3,000,000 or more different nucleic acid hybridizations.

The term "microtiter plates" as used herein refers to arrays of discrete wells that come in standard formats (96, 384 and 1536 wells) which are used for examination of the physical, chemical or biological characteristics of a quantity of samples in parallel.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Perfect match: The term "match," "perfect match," "perfect match probe" or "perfect match control" refers to a nucleic acid that has a sequence that is designed to be perfectly complementary to a particular target sequence or portion thereof. For example, if the target sequence is 5'-GATTGCATA-3' the perfect complement is 5'-TATGCAATC-3'. Where the target sequence is longer than the probe the probe is typically perfectly complementary to a portion (subsequence) of the target sequence. For example, if the target sequence is a fragment that is 800 bases, the perfect match probe may be perfectly complementary to a 25 base region of the target. A perfect match (PM) probe can be a "test probe", a "normalization control" probe, an expression level control probe and the like. A perfect match control or perfect match is, however, distinguished from a "mismatch" or "mismatch probe."

Mismatch: The term "mismatch," "mismatch control" or "mismatch probe" refers to a nucleic acid whose sequence is deliberately designed not to be perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at the center of the probe, for example if the probe is 25 bases the mismatch position is position 13, also termed the central position, such that the mismatch is most likely to destabilize the duplex with the target sequence under the test hybridization conditions. A homo-mismatch substitutes an adenine (A) for a thymine (T) and vice versa and a guanine (G) for a cytosine (C) and vice versa. For example, if the target sequence was: 5'-AGGTCCA-3', a probe designed with a single homo-mismatch at the central, or fourth position, would result in the following sequence: 3'-TCCTGGT-5', the PM probe would be 3'-TCCAGGT-5'.

The term "target sequence", "target nucleic acid" or "target" refers to a nucleic acid of interest. The target sequence may or may not be of biological significance. Typically, though not always, it is the significance of the target sequence which is being studied in a particular experiment. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc.

Target sequences may be interrogated by hybridization to an array. The array may be specially designed to interrogate one or more selected target sequence. The array may contain a collection of probes that are designed to hybridize to a region of the target sequence or its complement. Different probe sequences are located at spatially addressable locations on the array. For genotyping a single polymorphic site probes that match the sequence of each allele may be included. At least one perfect match probe, which is exactly complementary to the polymorphic base and to a region surrounding the polymorphic base, may be included for each allele. In a preferred embodiment the array comprises probes that include 12 bases on either side of the SNP. Multiple perfect match probes may be included as well as mismatch probes.

Hybridization probes are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics. See U.S. patent application Ser. No. 08/630,427.

C. Mouse Exon Arrays

The RNA transcripts of most eukaryotic genes undergo a series of processing reactions. Often this involves removal of unwanted internal segments and rejoining of the remaining segments in a process termed RNA splicing. The 5' and 3' ends of the transcripts are typically also processed by, for example, capping at the 5' end and polyadenylation of the 3' end. The resulting processed transcript will correspond to the expression product, which may be either a polypeptide or a noncoding RNA. Generally for vertebrate genes, only a small portion of the sequence of the gene is used to generate the final product. For most genes, the genetic information that will be present in the final transcript (exons) is separated by intervening sequences that do not contribute genetic information directly to the final product (introns) and are typically removed during processing of the primary transcript to the mature transcript. For genes that contain multiple exons the primary transcript contains sequences that are complementary to both the exons and introns of the gene. The RNA transcript undergoes splicing, a process that excises the introns and joins the exons.

The signals that define the boundaries of introns and exons are not completely understood so predicting exons and introns from primary sequence is difficult. Many introns start with GT (GU in the RNA) and end with AG (GT-AG rule), but this alone is not sufficient to define introns and there is at least one other minor class of introns that start with AT and end with AC (AU-AC spliceosome), see Tarn and Steitz, *Trends Biochem. Sci.* 22:132-137 (1997). Introns also contain a conserved branch site that includes an A residue.

Processing of primary transcripts, along with the possible use of alternative promoters and alternative polyadenylation sites, allows a single gene to generate many different mature RNA isoforms, by varying the pattern of splicing in a process known as alternative splicing. In this way a single gene may generate a dozen or more different mRNAs.

The human dystrophin gene is one example where different promoters are used to to generate different protein isoforms. The gene has at least 7 different promoters that can be used and has at least 79 exons. Three of the promoters are near the conventional start site. One is used in brain-cortex, another is muscle-specific and the third is used in Purkinje cells of the cerebellum. Each promoter results in the inclusion of a different exon 1 in the mature transcript. The other 4 promoters result in shorter forms that are lacking upstream exons so that each generates a progressively smaller isoform. Alternative splicing is also known to occur in the 3' end of the gene.

It is currently thought that more than half of all human genes are alternatively spliced, allowing alternative pre-mRNA splicing to account for much of the diversity of the proteins present in human cells. See, for example, Lareau et al. *Curr. Op. Struct. Biol.* 14:273-282 (2004), Boue et al, *Bioessays* 25:1031-1034 (2003), Modrek and Lee, *Nat. Genet.* 30:13-19 (2002), Mironov et al., *Genome Res* 9:1288-1293 (1999), and Modrek et al., *Nucleic Acid Res.* 29:2850-2859 (2001). Other mammals such as rats and mice have similar levels of alternative splicing. Alternative splicing functions as a regulatory process that generates biological complexity by controlling the expression of proteins.

Variation in mRNA structure may result from, for example, intron retention, competing 5' splice sites, competing 3' splice sites, multiple promoters, multiple poly(A) sites, cassette exons (exon skipping) and mutually exclusive exons. See, Roberts and Smith, *Curr. Opin. Chem. Biol.* 6:375-383 (2002). These changes may be regulated, for example, depending on tissue type, sexual genotype, cellular differentiation or activation of cell signaling pathways.

An example of the use of mutually exclusive exons is shown in FIG. 1. The primary transcript (100) contains 4 exons, exons 1-4. The transcript can be spliced to generate a first RNA isoform (103) or a second RNA isoform (105). The first (103) and second (105) isoforms both contain exons 1 and 4. The first isoform contains exon 3 but not exon 2 and the second isoform contains exon 2 but not exon 3. A probe to exon 1 (110) and a probe to exon 4 (120) will hybridize to both isoforms, while a probe to exon 3 (115) will hybridize to the first isoform and not the second and a probe to exon 2 (140) will hybridize to the second isoform and not the first. Probes (115) and (140) may be used to differentially detect the two isoforms while probes (110) and (120) may be used to detect both isoforms but will not distinguish between the two isoforms.

In one aspect probe arrays that have probe sets that are complementary to individual exons or subsequences of exons are disclosed. Probe sets may have 1, 2, 3, 4, 5, 6, 7 to 10 or more probes. Each probe in the probe set may differ from the other probes in the probe set by at least one base. The probes in a probe set are perfectly complementary to different regions of the same predicted exon or subsequence of an exon. In preferred aspects the probes in a given probe set are selected so that they may be used to detect the presence or absence of a specific exon in RNA. Arrays of probes are disclosed that allow for simultaneous measurement of relative gene expression levels mouse genes, including detection and measurement of multiple isoforms of mature RNA generated from the same gene. Many of the probes of the array are designed to be complementary to about 25 contiguous bases of a selected exon or exon subsequence. Mismatch probes may be included on the array for use as controls to measure discrimination and specificity. Antisense probes that are derived from the opposite strand of the gene may also be included. Other control sequence probes may also be included. For example, control probes may be included to assay for manufacturing defects, problems with sample preparation and problems with hybridization.

Splicing analysis using microarrays has been reported by, for example, Clark et al. *Science* 296: 907-910 (2002) and Johnson et al. *Science* 302: 2141-2144, which are both incorporated herein by reference in their entireties. See also Modrek and Lee, Nature Genet. 30:13*19 (2002). It has been estimated that approximately 15% of disease-causing single point mutations may affect splicing. See Krawczak et al. *Hum. Genet.* 90:41-54 (1992).

In one aspect the array includes a probe set for each exon in each of at least 1,000, 2,000, 3,000, 5,000, 10,000, 15,000, 20,000 or 25,000 human genes. The array may include a probe set for each exon in each of at least 1,000, 2,000, 3,000 or 5,000 genes that each have at least 2, 3, 4, or 5 to 10 exons. Previous array designs utilized amplification methods that resulted in a bias toward the amplification of the 3' end of the RNA and probe sets were directed at regions that were within about 600 bases of the 3' end of the mRNA. This typically includes 3' UTR and the most 3' exon or exons. Probes to exons that were nearer to the 5' end of the RNA were not included unless the RNA was short, for example, less than 600 bases. The WTA and small WTA methods of amplification of RNA utilize random primers and are therefore not as biased toward the 3' end of the RNA as methods that use oligo dT primers. Using unbiased amplification methods all exons of a gene may be detected and probes are accordingly designed to detect exons throughout the RNA and including the 5' exons.

The arrays may be used, for example, to identify and measure tissue-specific alternative splicing, to verify the existence of splice variants, to identify novel splice variants and to estimate gene expression levels. Hybridization intensity data from exon, junction, gene and unique probes can be deconvoluted using a computer system and the used to determine the expression levels of alternatively spliced forms of mouse genes. Different mature RNA isoforms may contain different exons or portions of exons-resulting from the use of alternative splice sites within an individual exon or from use of alternative promoter or poly (A) sites.

In a preferred embodiment an array of probes is disclosed and the array comprises a plurality of different features. A different probe sequence is synthesized in each feature. Each feature may have many copies, for example more than 1,000,000 copies, of the probe sequence. Probes of the array have sequences corresponding to the sequences in the sequence listing, SEQ ID NOs 1-991,174. SEQ ID NOs 1-72114 and 495,674-852095 are exon probes. SEQ ID NOs 72115-155,804 are gene probes. SEQ ID NOs 155,805-399, 413 and 852,096-991,174 are junction probes. SEQ ID NOs 399,414-495,673 are unique probes. In one embodiment SEQ ID NOs 1-495,673 are immobilized on a first solid support (chip A) and probes 495,674-991,174 are immobilized on a second solid support (chip B). Arrays comprising 100,000, or more probes selected from the sequence listing are also contemplated.

Different types of probes may be included on an array. In one embodiment "exon", "gene", "junction" and "unique" probes may be included. Exon probes are complementary to exon regions and an exon probe set may include probes that are complementary to different exons so that more than one exon of a transcript may be represented by an exon probe set. Gene probes hybridize to spliced forms of genes in regions that are present in all known spliced forms. Junction probes hybridize to the junction between two exons after the intron has been removed by splicing. In a preferred embodiment the junction probes of the array hybridize to alternatively spliced junctions. In a preferred embodiment a probe set consists of 6 probe pairs for a junction. The probes vary in the position of the central position, for example one probe pair may have the central or 0 position of the probe correspond to the last base of the upstream exon and other probes in the set are then shifted upstream or downstream so that the central position of the probe corresponds to a base that is upstream or downstream of the junction. Probes may be positioned, for example, at 0, −1, −2, −3, −5, +1, +2 and +4 relative to the junction, see Wang et al. Bioinformatics p 1-5 (2001). Unique probes detect a single form of an alternatively spliced gene or a subset of forms. Unique probes can be used to detect the presence of specific alternatively spliced gene products. Combining different types of probes on an array provides increases sensitivity, specificity, information and assay potential.

In one embodiment an array comprising a subset of SEQ ID NOs 1-991,174 is disclosed. The subset preferably includes at least 100,000 different sequence probes wherein each probe is one of the sequences of SEQ ID NOs 1-991, 174. The probes may be attached to a single solid support so they can be monitored simultaneously in a single experiment or the probes may be divided so that they are on two or more chips or solid supports. The arrays may also be attached to pegs for high throughput analysis.

SEQ ID Nos. 1-991,174, encompassed in the Sequence listing, represent probe sequences that may be included in aspects of the invention. In one aspect the complement of the probe may be included on the array. In a preferred aspect the complement is the perfect complement of the probe and is the same length as the probe. For example, if the probe is 5'-ggtagcatc-3' the perfect complement is 5'-gatgctacc-3'. In one aspect a mismatch probe corresponding to the provided probe sequence is included on the array for a plurality of the probes. The mismatch probe may be identical to the probe except for a change at the central base, position 13 of a 25 base probe.

In one aspect an array that includes at least 100,000 different features wherein each feature includes a different sequence probe that contains at least 15 nucleotides from one of the sequences listed in SEQ ID NO: 1-991,174 is provided. In one aspect the probes may be longer than the sequence provided in the sequence listing, for example, the probes may be 26 to 100 bases in length. The additional sequence may be sequence that is immediately adjacent to the provided sequence in the human genome, for example, bases that are immediately upstream of downstream of the provided sequence. Preferably the probe is complementary to 15 to 100 contiguous bases in the human genome.

Figure 2:
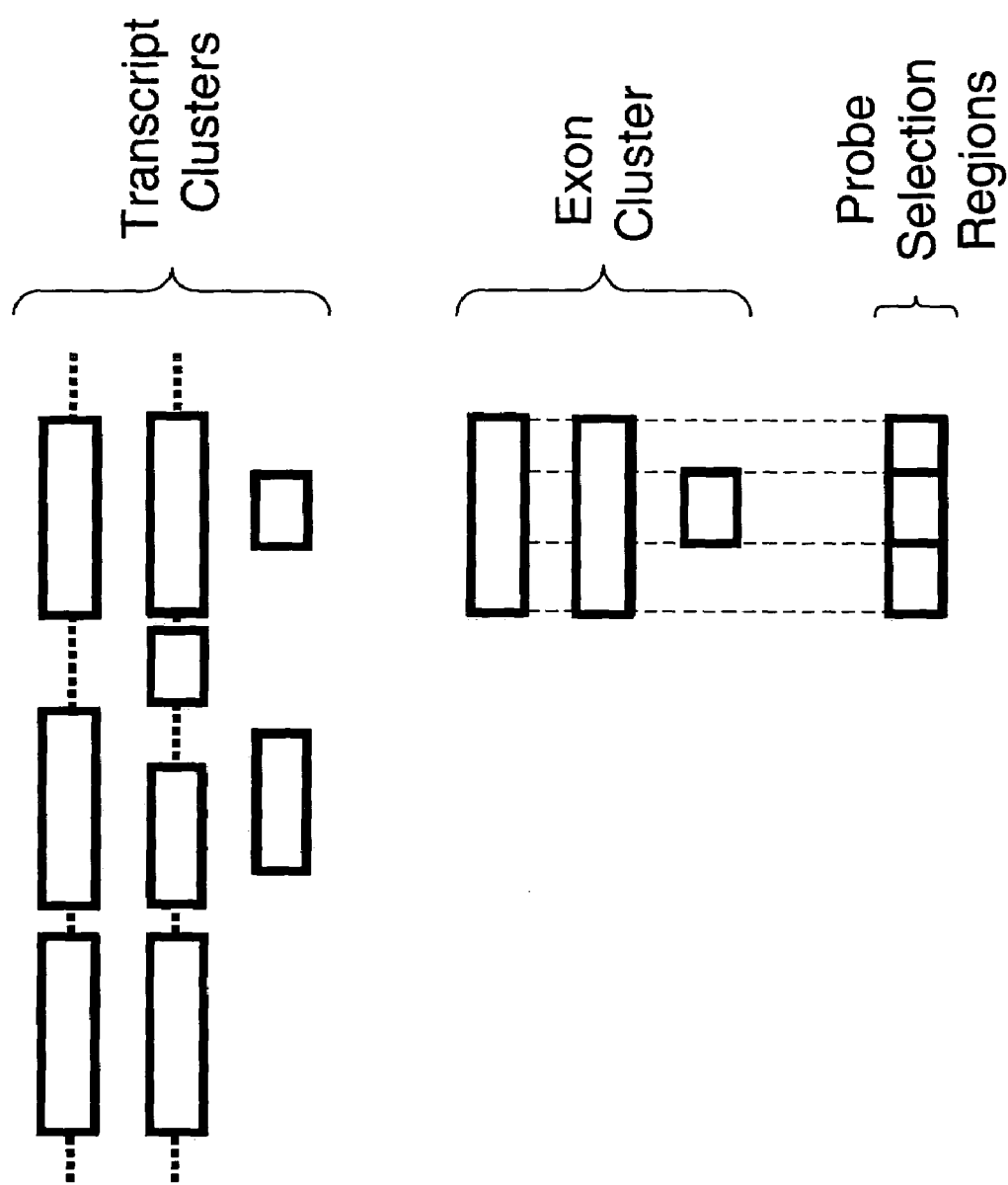
FIG. 2 shows examples of transcript clusters, exon clusters and probe selection regions. Individual probe sets are designed to be detect individual probe selection regions. A transcript cluster may be represented by many probe sets each corresponding to different probe selection regions. Transcript clusters may include multiple exon clusters.
Figure 3:
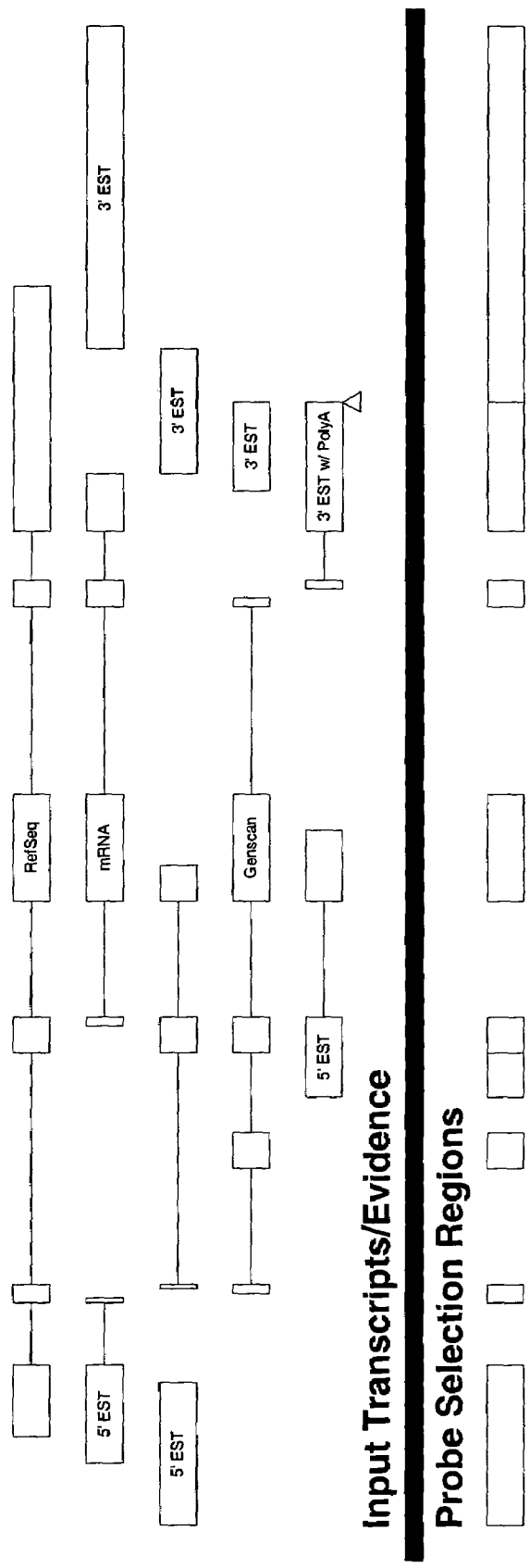
FIG. 3 shows a series of input transcript evidence from a number of sources and the output probe selection regions.

In one aspect probes were selected for the array by consolidating input sequences and annotations onto the mouse genome and into transcript clusters. Exon clusters were identified from the transcript clusters and Probe Selection Regions (PSRs) were identified from the exon clusters (FIG. 2). Individual probe sets were designed to be complementary to the PSRs. Each probe set including at least 4 different probes that are complementary to the same PSR. The probes in a probe set may overlap but differ from each of the other probes in the probe set by at least one base. The PSRs were selected to have the property that they are contiguous and do not overlap in genome space. An example of PSRs resulting from the consolidation process is shown in FIG. 3. A collection of input annotations from a plurality of sources were projected onto the genome to infer transcribed regions. Internal splice sites, polyadenylation sites (indicated by triangle) and CDS start and stop positions may be used to infer "hard edges" which are may be used to define the boundary of a PSR. This may result in the fragmentation of a contiguous piece of transcribed sequence (an exon cluster) into multiple PSRs. Each PSR may represent a different possible splicing or processing event or it may be the result of errors in the available annotations. Exon clusters may be further grouped into transcript clusters based on overlapping boundaries of input annotations. A transcript cluster may include more than one gene if the genes overlap. A gene may also be split into multiple transcript clusters if there is fragmented evidence of the gene in the input data source.

Many annotations are incomplete at the 5' or 3' end so in many aspects the outer boundary of a transcript are not treated as hard edges for the boundary of a PSR. A single gene that has, for example, 10 exons, may be represented on the array by more than 10 probe sets, each probe set being complementary to a different PSR. One or more of the exons may be divided into two or more PSRs based on variable evidence of the boundary of the exon in the input data.

Probe sequences were chosen to detect alternative splicing in mouse genes. Probe sequences listed in SEQ ID NOS 1-991,174 corresponds to sequences in the GenBank database. The GenBank sequence database may be searched through the use of computer programs such as BLAST to identify the region of the genome that is complementary to a probe. Access to BLAST is available to the public through the internet at, for example, http://www.ncbi.nim.nih.gov. One of skill in the art will be familiar with the use of the BLAST program to obtain information about particular sequences in order to, for example, determine the GenBank accession number, determine the gene from which the sequence is derived, to determine other genes and species which contain similar sequences and to determine the degree of similarity between one sequence and another.

When measuring expression one of skill in the art will recognize that the probes of the array should be designed to be complementary to the sequence to be detected. This may vary depending on which amplification method is used. For example, one method of amplification calls for reverse transcription of the mRNA using an oligo-dT-T7 primer. Double stranded cDNA with an RNA polymerase promoter is then generated and antisense RNA is transcribed and labeled. The antisense RNA is then hybridized to the array. The antisense RNA is complementary to the mRNA so the sense probe on the array that is designed to hybridize to the antisense RNA is identical in sequence to a portion of the starting mRNA. In another method the amplified RNA to be hybridized to the array is sense, meaning that it has the same sequence as the starting mRNA. In other embodiments the amplification product that is hybridized to the array may be cDNA that may be of the sense (same as) or antisense (complement of) orientation relative to the starting mRNA.

In preferred embodiments the mRNA to be analyzed is amplified and labeled using an amplification method that has reduced bias of amplification. Methods of amplification may preferentially amplify selected regions of nucleic acid, for example, amplification of mRNA using oligo-dT primers preferentially amplifies the 3' end of mRNA because reverse transcription is always primed from the 3' end. Methods that prime reverse transcription using random primers, for example, show reduced bias toward the 3' end of mRNA. Other methods for amplification are disclosed in U.S. Patent Application Nos. 60/498,023, 60/495,232 and 10/090,320 which are each incorporated herein by reference in their entireties.

In one aspect the RNA to be analyzed is reverse transcribed in a first cycle to generate first strand cDNA using a T7-(N)$_6$ primer. The primer may include a 5' T7 promoter sequence and a 3' random segment. Second strand cDNA is then synthesized and cRNA is generated by in vitro transcription using T7 RNA polymerase and un-labeled ribonucleotides. The cRNA (antisense RNA), which may first be cleaned, is then used in a second cycle to synthesize a second round of first strand cDNA using random primers and in the presence of dUTP. Then second strand cDNA is synthesized also in the presence of dUTP. The double stranded cDNA from the second cycle, with dUTP incorporated is fragmented using uracil DNA glycosylase and an AP endonuclease, such as APE 1. The fragments may be end labeled with a biotin-labeled compound in the presence of terminal deoxytransferase. The labeled fragments may be hybridized to an array. In some aspects polyadenylated controls are added to the total RNA sample prior to the first cycle first strand cDNA synthesis step.

The present invention provides a pool of unique nucleotide sequences complementary to alternatively spliced mouse sequences in particular embodiments which alone, or in combinations of 1,000 or more, 10,000 or more, or 100,000 or more, can be used for a variety of applications. Probe sets are complementary to a single exon or to a subsequence of an exon. Genes with more than one exon are represented on the array by more than one probe set, each probe set being complementary to a different exon. For example, if a gene has 10 different exons the array will include preferably include a unique probe set for each of the 10 exons. In some aspects a single exon will be represented by more than one probe set. Each different oligonucleotide may be a different feature of the array and each feature may be approximately 25, 18, 11, 8, 5, 2 or 1 microns square. The oligonucleotides may be 15 to 20, 21 to 25, 26 to 30, 31 to 40, 40 to 80 or 15 to 100 bases in length.

In one embodiment, the present invention provides for a pool of unique nucleotide sequences which are complementary to alternatively spliced mouse mRNAs formed into a high density array of probes suitable for array based massive parallel gene expression. Array based methods for monitoring gene expression are disclosed and discussed in detail in U.S. Pat. Nos. 5,800,992, 6,309,822, and PCT Application WO 92/10588 (published on Jun. 25, 1992), all of which are incorporated herein by reference for all purposes. Generally those methods of monitoring gene expression involve (1) providing a pool of target nucleic acids comprising RNA transcript(s) of one or more target gene(s), or nucleic acids derived from the RNA transcript(s); (2) hybridizing the nucleic acid sample to a high density array of probes and (3) detecting the hybridized nucleic acids and calculating a relative expression (transcription, RNA processing or degradation) level.

The development of Very Large Scale Immobilized Polymer Synthesis or VLSIPS™ technology has provided methods for making very large arrays of nucleic acid probes in very small arrays. See U.S. Pat. No. 5,143,854 and PCT Patent Publication Nos. WO 90/15070 and WO 92/10092, and Fodor et al., Science, 251, 767-77 (1991), each of which is incorporated herein by reference. U.S. Pat. No. 5,800,992, describes methods for making arrays of nucleic acid probes that can be used to detect the presence of a nucleic acid containing a specific nucleotide sequence. Methods of forming high density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling.

In a preferred detection method, the array of immobilized nucleic acids, or probes, is contacted with a sample containing target nucleic acids, to which a flourescent label is attached. Target nucleic acids hybridize to the probes on the array and any non-hybridized nucleic acids are removed. The array containing the hybridized target nucleic acids are exposed to light which excites the flourescent label. The resulting flourescent intensity, or brightness, is detected. Relative brightness is used to determine which probe is the best candidate for the perfect match to the hybridized target nucleic acid because flourescent intensity (brightness) corresponds to binding affinity. Once the position of the perfect match probe is known, the sequence of the hybridized target nucleic is known because the sequence and position of the probe is known.

In another embodiment, the current invention may be combined with known methods to monitor expression levels of alternatively spliced forms of genes in a wide variety of contexts. For example, where the effects of a drug on gene expression are to be determined, the drug will be administered to an organism, a tissue sample, or a cell and the gene expression levels will be analyzed. For example, nucleic acids are isolated from the treated tissue sample, cell, or a biological sample from the organism and from an untreated organism tissue sample or cell, hybridized to a high density probe array containing probes directed to the gene of interest and the expression levels of that gene are determined. The types of drugs that may be used in these types of experiments include, but are not limited to, antibiotics, antivirals, narcotics, anti-cancer drugs, tumor suppressing drugs, and any chemical composition which may affect the expression of genes in vivo or in vitro. The current invention is particularly suited to be used in the types of analyses described by, for example, pending U.S. Applications No. 6,309,822 and PCT Application No. 98/11223, each of which is incorporated by reference in its entirety for all purposes. As described in Wodicka et al., Nature Biotechnology 15 (1997), hereby incorporated by reference in its entirety for all purposes, because mRNA hybridization correlates to gene expression level, hybridization patterns can be compared to determine differential gene expression. As non-limiting examples: hybridization patterns from samples treated with certain types of drugs may be compared to hybridization patterns from samples which have not been treated or which have been treated with a different drug; hybridization patterns for samples infected with a specific virus may be compared against hybridization patterns from non-infected samples; hybridization patterns for samples with cancer may be compared against hybridization patterns for samples without cancer; hybridization patterns of samples from cancerous cells which have been treated with a tumor suppressing drug may be compared against untreated cancerous cells, etc. Zhang et al., Science 276 1268-1272, hereby incorporated by reference in its entirety for all purposes, provides an example of how gene expression data can provide a great deal of insight into cancer research.

In one embodiment, the current invention provides a pool of unique nucleic acid sequences which can be used for parallel analysis of gene expression and alternative splicing under selective conditions. Without wishing to be limited, genetic selection under selective conditions could include: variation in the temperature of the organism's environment; variation in pH levels in the organism's environment; variation in an organism's food (type, texture, amount etc.); variation in an organism's surroundings; etc. Arrays, such as those in the present invention, can be used to determine whether gene expression is altered when an organism is exposed to selective conditions.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. In a preferred aspect the amplification method results in a DNA target for hybridization and the DNA is fragmented and end labeled using a terminal transferase.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$p), phosphorescent labels, enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993), which is hereby incorporated by reference in its entirety for all purposes.

Arrays may be designed so that the array has probe sets that include 1, 2, 4 or 6 or more perfect match probes that are each complementary to a predicted exon of a gene. Many genes contain multiple exons and preferably a probe set is included for each exon. Probe sets may be designed to recognize a single exon or a single intron. An array with probe sets complementary to more than 5,000, 10,000, 30,000, 50,000, 75,000 or 100,000 exons is disclosed.

In one aspect a pool of unique nucleic acid sequences which are complementary to exons in mouse genes are disclosed. These sequences can be used for a variety of types of analyses, including analysis of alternative splicing and measurement of gene expression. An array to detect alternatively splicing, comprising probe sets to exons that are alternatively spliced is also disclosed. Some exons may have alternative 5' or 3' splice sites resulting in alternative forms of the exon being present in alternative spliced forms and probe sets may be designed to detect alternative forms of a single exon. Probe sets to detect retained introns, mutually exclusive exons, alternative promoter sites and alternative polyadenylation sites may also be included.

In one aspect probe sets are designed to be complementary to regions that are within exons or PSRs. In one aspect probe sets are designed to interrogate PSRs that are 25 bp or greater. In another aspect probe sets are also included for PSRs that are less than 25 bp. In another aspect splice events may be interrogated with junction probe sets. Exon junction probe sets include probes that spanning multiple exons which are not contiguous on the genome. Exon-intron junction probe sets span the junction between an exon and an intron. Junction probe sets may be used to detect specific splicing events such as the joining of a first and second exon. Some exons or PSRs may be very short, for example, 1, 2, 3 or 4-24 bp. These exons may be detected by junction probes that include the small exon or PSR and flanking exon sequence that is joined to the small exon or PSR by splicing. The junction probe spans the PSR and flanking sequence from the upstream or downstream PSR.

In one aspect probe coverage varies from gene to gene depending on how many exons (or more specifically PSRs) a gene has. As such, some single exon transcripts may have fewer than ten probes, although in the array described in Example 1 the majority of the putative full-length mRNAs are covered by 10 or more probes.

CONCLUSION

The inventions herein provide a pool of unique nucleic acid sequences which are complementary to alternatively spliced mouse genes. These sequences can be used for a variety of types of analyses.

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07341835B2). An electronic copy of the "Sequence Listing" will also be available from the USPTO upon request and payment of the fee set forth in 37 CFR 1.19(b)(3).

What is claimed is:

1. A probe array comprising a plurality of nucleic acid probes, wherein each probe in the plurality of nucleic acid probes consists of one of the sequences listed in SEQ ID Nos. 1-991,174 and wherein the plurality of nucleic acid probes of the array consists of each of the sequences listed in SEQ ID Nos. 1-991,174, each sequence present as a different feature of the array.

2. The array of claim 1 wherein said plurality of nucleic acid probes is attached to a solid support.

3. The array of claim 1 wherein the array comprises a plurality of beads wherein the probes are attached to the beads and the probes on a bead consisting of one of the sequences listed in SEQ ID Nos. 1-991,174.

4. The probe array of claim 1 wherein the array consists of a single contiguous solid support.

5. The probe array of claim 1 wherein the array consists of a plurality of solid supports.

6. A kit comprising a probe array according to claim 1, a T7-N6 primer, random primers, a T7 RNA polymerase, dUTP, UDG and optionally an AP endonuclease.

7. A method of detecting a plurality of mature RNA isoforms from each of a plurality of mouse genes in a biological sample from a mouse comprising:
   obtaining a nucleic acid derived from the biological sample;
   labeling the nucleic acid;
   hybridizing the labeled nucleic acid to the array of claim 1;
   detecting the hybridization pattern; and
   analyzing the hybridization pattern to detect a plurality of mature RNA isoforms from at least two mouse multi exon genes.

8. The method of claim 7 wherein the labeled nucleic acid hybridized to the array consists essentially of DNA.

9. The method of claim 7 wherein the labeled nucleic acid hybridized to the array consists essentially of RNA that is complementary to the target mRNA.

10. The method of claim 7 wherein the labeled nucleic acid hybridized to the array consists essentially of RNA that is in the sense orientation relative to the target mRNA.

* * * * *